United States Patent [19]
Wan et al.

[11] 3,952,352
[45] Apr. 27, 1976

[54] ELECTRONIC STROKE EFFECTIVENESS SENSOR FOR COMPETITIVE SWIMMERS

[76] Inventors: Lawrence A. Wan; Sara J. Wan, both of 17819 Joshua Circle, Fountain Valley, Calif. 92708

[22] Filed: May 2, 1975

[21] Appl. No.: 573,876

[52] U.S. Cl. ............................................ 9/307; 9/308
[51] Int. Cl.² ............................................ A63B 31/02
[58] Field of Search ...................... 9/301, 307, 308; 272/71; 128/2.1 A, 25

[56] References Cited
UNITED STATES PATENTS

| | | |
|---|---|---|
| 3,174,167 | 3/1965 | Pauley ................................. 9/308 |
| 3,478,344 | 11/1969 | Schwitzgebel et al. .......... 128/2.1 A |

*Primary Examiner*—Trygve M. Blix
*Assistant Examiner*—Stuart M. Goldstein

[57] ABSTRACT

A bodyworn apparatus that senses and measures the hydrodynamic thrust generated by a swimmer's hands as he strokes his hands through the water. The apparatus consists of pressure sensitive transducers that convert the amount of thrust into electric signals that are fed back to the swimmer in terms of an audio tone with tone frequency varying as a function of thrust and/or are transmitted to a recording instrument calibrated to quantitatively meter and record the thrust generated by the swimmer's arm strokes.

5 Claims, 3 Drawing Figures

ELECTRONIC STROKE EFFECTIVENESS SENSOR FOR COMPETITIVE SWIMMERS

BACKGROUND OF THE INVENTION

This invention pertains to the stroke training of competitive swimmers. The basic principle of an effective stroke is to move the arm and hand in such a manner as to generate the most forward thrust throughout all the phases of the hand and arm positions of each official style of stroke. To accomplish this, the swimmer must vary the speed, and position (location and orientation) of his hands and arms at different stages of the stroke. The ultimate objective therefore, is to determine the optimum variations, i.e., stroke form, for the swimmer. This means that the thrust generated must be sensed or determined.

Prior art devices for sensing thrust have all been in the form of hand paddles, as in U.S. Pat. Nos. 3,765,042, 3,698,026, 2,812,138, and 3,397,414, whereby, the swimmer's sensitivity to the position of the hand and the thrust delivered is supposed to be accentuated by the additional amount of water the paddle is able to catch compared to the bare hand, and by the slippage and resistance of the paddle as it is moved correctly or incorrectly through the water. Aside from the fact the actual effectiveness of such paddle devices is yet undetermined and is disputed among coaches vis-a-vis the multitude of controversy over the manner the paddle should be strapped to the hand, such prior art devices possess the following critical disadvantages.

a. There is no absolute measure of the actual thrust generated in quantitative physical units.
b. Providing no absolute or even direct measurement of the thrust, a swimmer is not given any information as to whether or not the maximum thrust the swimmer is capable of generating is actually achieved.
c. There is no way a coach on the pool deck can remotely ascertain how effective the swimmer is stroking.
d. The arm of the swimmer is also capable of contributing to the thrust, yet the paddles in no way indicate the propulsion generated by any part of the arm.
e. The best the paddles can do is to accentuate the sense of touch in giving the swimmer an indication of stroke effectiveness. This is one of man's least reliable senses and therefore no real positive feedback is provided to the swimmer If the swimmer has a sharp sense of touch with respect to the water, a rare ability, paddles will contribute nothing more.

It is, therefore, an object of the present invention to provide a stroke training apparatus which avoids the aforementioned problems of the prior art.

A further object of the present invention is to provide an electronic device with transducers worn on the swimmer's hand and/or arm that translates the amount of hydrodynamic thrust generated by a swimmer's arm and/or hand into electrical signals.

Still a further object of the present invention is to provide the swimmer with a direct and positive feedback as to the thrust his stroke is generating by an electronic device that transforms the electric signals generated by the above mentioned transducers into an audio frequency tone that varies in frequency as a function of the amount of thrust generated as he is stroking, and the tone is heard by the swimmer through a miniature earpiece speaker.

Yet, another object of the present invention is to provide the swimmer with an audio signal feedback while swimming so the swimmer can find, learn, and develop the indivdualized stroke style that achieves the maximum thrust for forward propulsion that a given individual is capable of as a function of his particular physiology, for each official competitive stroke.

Still another object of the present invention is to provide an electronic device worn by the swimmer that transmits by radio frequency, the electric signals from the transducers to a remote monitor on the pool deck that records, meters, and graphs the thrust delivered throughout the swimmer's stroke in quantitative units of measure or coach analysis and instruction.

These and other objects, features and advantges will, in part, be pointed out with particularity and will, in part, become obvious from the following more detailed description of the invention taken in conjunction with the accompanying drawings which form an integral part thereof.

DESCRIPTION OF THE SHOWN EMBODIMENT

Figure 1:
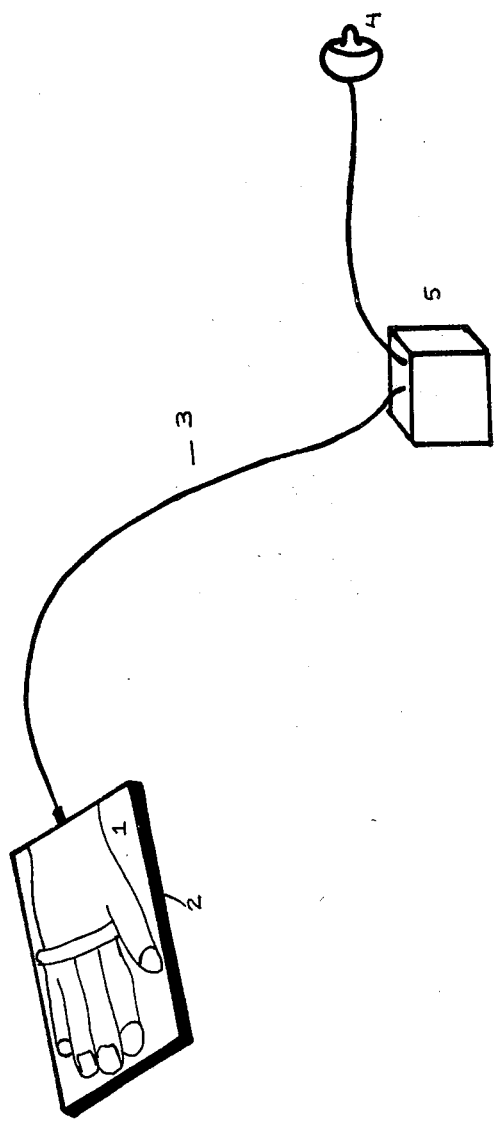
FIG. 1 shows the main elements of the paddle sensor system.
Figure 3:
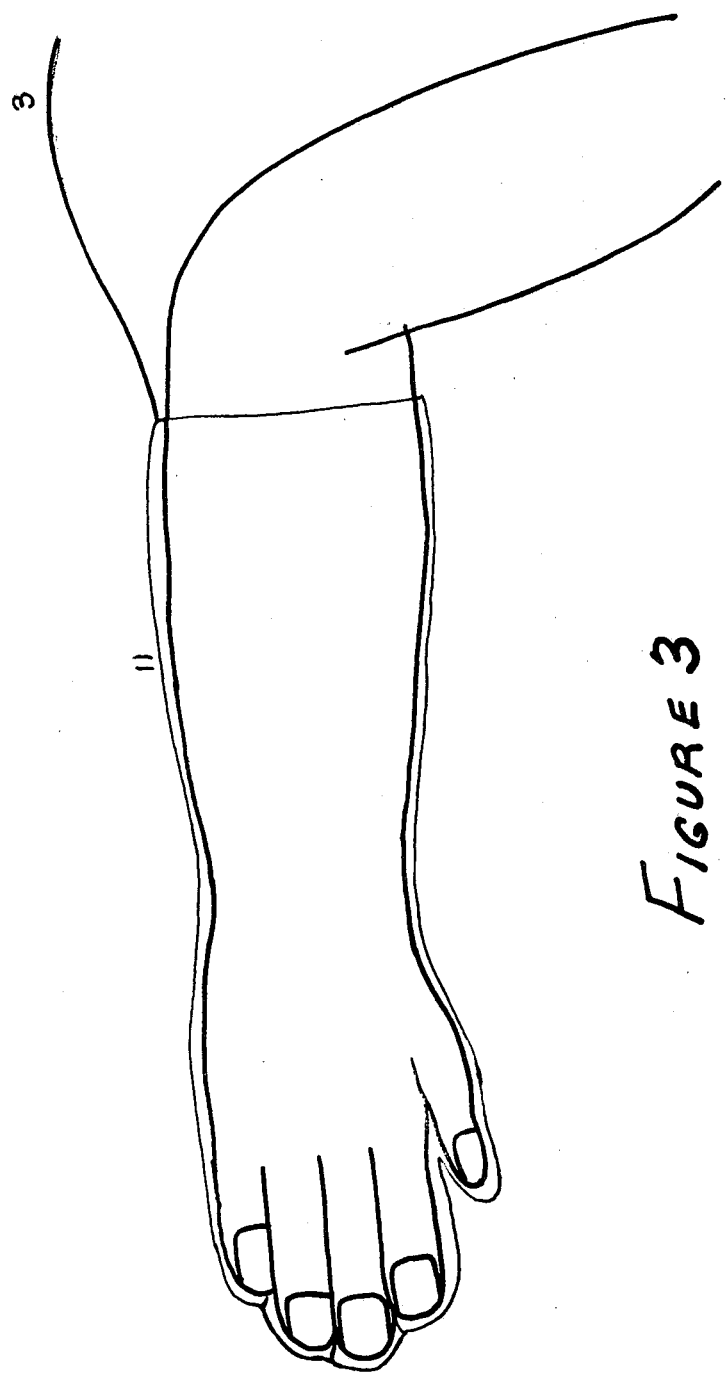
FIG. 3 shows an alternate sensor carrying element.

Reference is made to FIG. 1, wherein is shown one form of embodiment. A paddle 1 of acrylic plastic sheet material as in conventional swim paddles is strapped to the hand by stretch on bands in conventional swim paddle fashion. On the underside of the paddle is a layer of pressure sensitive material 2. Such material can be compressible rubber impregnated with conductive carbon such that the electrical resistance of said material varies as a function of compression. The carbon microphone in the telephone operates by the same principle. Reference is made to FIG. 3 where alternatively the impregnated transducer rubber material can be in the form of a stretch-on arm length glove 11 to include the thrust contributed by the arm as well. The material is connected by flexible cable 3 stretched along the arm to a bodyworn waterproof small electronic battery powered package 5. Said package contains an audio oscillator generating a tone. The frequency of the tone is determined by a resistance capacitance circuit. The resistance in said circuit includes the resistive value of the conductive material on the paddle. As the material is compressed by the hand moving through the water. The resistance is changed and the frequency of the tone is changed. Thus, the pitch in the tone indicates the amount of water against paddle pressure that is generated. The package also contains an audio amplifier that amplifies the tone into an earpiece speaker 4 worn by the swimmer so the swimmer can hear the tone. Therefore, by listening the pitch of the tone as he strokes his hand through the water he is receiving audio feedback as to the amount of thrust he is delivering against the water.

Figure 2:
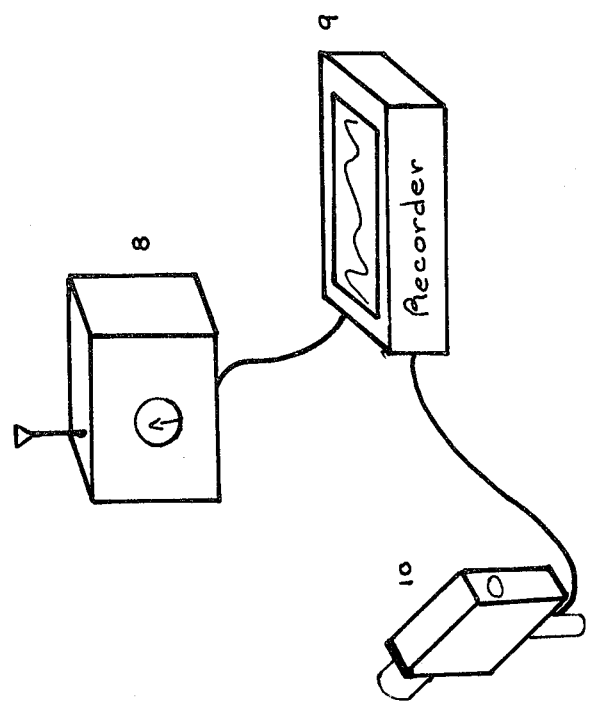
FIG. 2 shows the transmitting and recording elements of the system.
Figure 2:
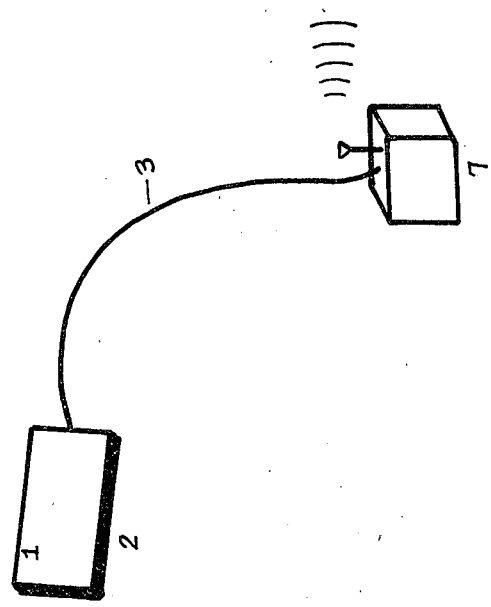

Reference is made to FIG. 2, wherein is shown a form of embodiment where the body worn electronic package further contains a radio transmitter 7 that transmits a modulation signal with signal amplitude varying as a function of the varying resistance value due to compression. This signal is received on pool deck by a receiver 8 and read out on a meter calibrated to indicate the actual value of the thrust delivered in quantitative units. Connected also is a recorder 9 that plots the measurement. Connected simultaneously is a video tape camera 10 so that the actual swimming stroke is visually recorded in synchronization with the thrust measurement. Thereby a total history of the stroking action is recorded, measured and monitored for analysis and coaching.

What we claim as new and desire to secure by Letters Patent is:

1. A hand and/or arm worn apparatus that senses and measures the propulsion generated in water by a swimmer's arm stroke as the swimmer strokes through the water comprising of:
   a. pressure sensitive transducers worn on the hand and/or arm that convert the thrust generated by the arm stroke as water pressure is created against the transducers into electric signals,
   b. a miniature electronic battery powered package worn on the swimmer that generates an audible tone into the swimmer's ear through a small earpiece such that the tone frequency or pitch is heard by the swimmer and varies directly as a function of the water pressure as thrust is generated against the transducers to give the swimmer a feedback indication of the effectiveness of his stroke form in delivering propulsion through the water, and
   c. a miniature radio transmitter worn on the swimmer's body that transmits the signals from the transducer to a remote pool-side meter and recorder to provide remote monitoring, measurement, and recording of the thrust generated in quantitative units.

2. An apparatus as in claim 1 where said pressure sensitive transducers are worn by the swimmer by means of a hand paddle, the transducers being placed on the surface of the paddle.

3. An apparatus as in claim 1 where said pressure sensitive transducers are worn by the swimmer by means of a stretch-on arm length glove with transducers in the material of the glove.

4. An apparatus as in claim 1 wherein said battery powered package includes electronic audio tone generator means, the tone frequency varying as a function of the electric signals from the pressure sensitive transducers.

5. An apparatus as in claim 1 including means for video taping the action of the arm stroke while simultaneously recording the arm stroke thrust.

* * * * *